US 9,778,184 B2

(12) United States Patent
Tamura et al.

(10) Patent No.: US 9,778,184 B2
(45) Date of Patent: Oct. 3, 2017

(54) MEASUREMENT METHOD AND MEASUREMENT DEVICE

(71) Applicant: KONICA MINOLTA, INC., Chiyoda-ku, Tokyo (JP)

(72) Inventors: Tsuruki Tamura, Tokyo (JP); Makiko Ootani, Tokyo (JP); Youichi Aoki, Saitama (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 15/120,505

(22) PCT Filed: Feb. 23, 2015

(86) PCT No.: PCT/JP2015/055009
§ 371 (c)(1),
(2) Date: Aug. 19, 2016

(87) PCT Pub. No.: WO2015/129615
PCT Pub. Date: Sep. 3, 2015

(65) Prior Publication Data
US 2017/0016823 A1    Jan. 19, 2017

(30) Foreign Application Priority Data
Feb. 25, 2014 (JP) .................................. 2014-033961

(51) Int. Cl.
G01N 21/47     (2006.01)
G01N 21/552    (2014.01)
(Continued)

(52) U.S. Cl.
CPC ......... *G01N 21/554* (2013.01); *G01N 21/553* (2013.01); *G01N 21/648* (2013.01);
(Continued)

(58) Field of Classification Search
CPC .. G01N 21/553; G01N 21/648; G01N 21/554; G01N 21/6428; G01N 33/54373; G01N 33/553; G01N 2021/6439
(Continued)

(56) References Cited

U.S. PATENT DOCUMENTS 6,194,223 B1   2/2001   Herrmann et al.
7,910,352 B2   3/2011   Miller et al.
(Continued)

FOREIGN PATENT DOCUMENTS

JP    10307141 A    11/1998
JP    2001272403 A  10/2001
(Continued)

OTHER PUBLICATIONS

International Search Report (ISR) and Written Opinion dated May 19, 2015 issued in International Application No. PCT/JP2015/055009.
(Continued)

*Primary Examiner* — Tarifur Chowdhury
*Assistant Examiner* — Isiaka Akanbi
(74) *Attorney, Agent, or Firm* — Holtz, Holtz & Volek PC

(57) ABSTRACT

With a blood-derived specimen on top of a metal film on a measurement chip, the intensity of reflected excitation light, the resonance angle of excitation light, the intensity of plasmon-scattered light, or the enhancement angle of excitation light is measured, and the acquired measurement is used to obtain a whole-blood hematocrit value. Using the obtained whole-blood hematocrit value, a first signal value that indicates how much of an analyte the specimen contains is converted to a second signal value that indicates how much of said analyte the liquid part of the specimen contains.

4 Claims, 6 Drawing Sheets

(51) Int. Cl.
*G01N 21/64* (2006.01)
*G01N 33/543* (2006.01)
*G01N 33/553* (2006.01)

(52) U.S. Cl.
CPC ... *G01N 21/6428* (2013.01); *G01N 33/54373* (2013.01); *G01N 33/553* (2013.01); *G01N 2021/6439* (2013.01)

(58) Field of Classification Search
USPC .................................................. 356/445–446
See application file for complete search history.

(56) References Cited

U.S. PATENT DOCUMENTS

| | | |
|---|---|---|
| 8,168,439 B2 | 5/2012 | Miller et al. |
| 8,309,364 B2 | 11/2012 | Miller et al. |
| 8,460,922 B2 | 6/2013 | Miller et al. |
| 8,808,626 B2 | 8/2014 | Miller et al. |
| 9,535,004 B2 * | 1/2017 | Noda ..................... G01N 21/13 |
| 2006/0160164 A1 | 7/2006 | Miller et al. |
| 2013/0078146 A1 * | 3/2013 | Sando .................. G01N 21/648 422/69 |
| 2013/0175457 A1 * | 7/2013 | Wada .................. G01N 21/648 250/459.1 |
| 2015/0025341 A1 | 1/2015 | Sakota et al. |
| 2016/0370289 A1 * | 12/2016 | Hikage ................ G01N 21/648 |

FOREIGN PATENT DOCUMENTS

| | | |
|---|---|---|
| JP | 2009085825 A | 4/2009 |
| JP | 2011002468 A | 1/2011 |
| WO | 2013122072 A1 | 8/2013 |

OTHER PUBLICATIONS

International Preliminary Report on Patentability and Written Opinion dated Sep. 9, 2016 issued in counterpart International Application No. PCT/JP2015/055009.

* cited by examiner

MEASUREMENT METHOD AND MEASUREMENT DEVICE

TECHNICAL FIELD

The present invention relates to a measurement method and a measurement device for measuring the amount of a measurement object substance in a sample containing at least a part of blood by utilizing surface plasmon resonance.

BACKGROUND ART

In laboratory tests and the like, highly sensitive and quantitative measurement of a minute amount of a measurement object substance such as protein and DNA in blood would enable quick determination of patient's conditions for treatment. There is therefore a need for a method for quantitatively measuring the measurement object substance in blood with high sensitivity.

Examples of known methods for measuring the measurement object substance in blood with high sensitivity include a surface plasmon resonance (hereinafter abbreviated as "SPR") method and a surface plasmon-field enhanced fluorescence spectroscopy (hereinafter abbreviated as "SPFS"). These methods utilize a phenomenon in which surface plasmon resonance (SPR) occurs when a metal film is irradiated with light under a certain condition (see, for example, PTL 1).

For example, in SPFS, a capturing body (for example, primary antibody) which can be specifically coupled with a measurement object substance is fixed on a metal film, and a reaction site for specifically capturing the measurement object substance is formed. When a sample (for example, blood) containing the measurement object substance is provided to the reaction site, the measurement object substance is coupled with the reaction site. Next, when the capturing body (for example secondary antibody) labeled with the fluorescence material is provided to the reaction site, the measurement object substance coupled with the reaction site is labeled with the fluorescence material. When the metal film is irradiated with excitation light in that state, the fluorescence material which labels the measurement object substance is excited by the electric field enhanced by SPR, thus emitting fluorescence. Accordingly, the presence or the amount of the measurement object substance can be measured by detecting the fluorescence. In SPFS, a fluorescence material is excited by the electric field enhanced by SPR, and therefore the measurement object substance can be measured with high sensitivity.

Not only in the SPR method and the SPFS but also in methods other than the SPR method and the SPFS, at the time of measurement of a measurement object substance in liquid, the measurement value is normally represented by the mass of the measurement object substance per unit volume of the liquid, a signal amount corresponding to the mass, or the like. Accordingly, when blood is used as a sample, the measurement value is represented by the mass of the measurement object substance per unit volume of the liquid component (plasma or serum) in the blood, the signal amount corresponding to the mass or the like. Since the ratio of the liquid component in blood differs depending on the person, the measurement value of whole blood (blood) cannot be converted to the liquid component measurement value in a uniform manner. In view of this, when whole blood is used as a sample, the hematocrit value of the whole blood (the ratio of the volume of the blood cell in blood) is measured and the measurement value of the whole blood is converted to the measurement value of the liquid component (plasma or serum) with use of the hematocrit value. Examples of conventional methods of measuring the hematocrit value include the micro hematocrit method in which blood is centrifuged, a method of obtaining the hematocrit value from the electric conductivity of blood, and a method of obtaining the hematocrit value from the concentration of hemoglobin of hemolyzed blood (see, for example, PTL 2).

CITATION LIST

Patent Literatures

PTL 1
Japanese Patent Application Laid-Open No. 10-307141
PTL 2
Japanese Patent Application Laid-Open No. 2001-272403

SUMMARY OF INVENTION

Technical Problem

When the above-mentioned conventional methods of measuring the hematocrit value is employed in measurement methods and measurement devices utilizing SPR such as the SPR method and SPFS, it is necessary to additionally employ devices for measuring the hematocrit value such as centrifugal separators, measurement devices for the electric conductivity or the concentration of hemoglobin, and as a result, the manufacturing cost and the measurement cost increase.

An object of the present invention is to provide a measurement method and a measurement device which utilize SPR and can perform correction of the measurement value using the hematocrit value without employing additional devices.

Solution to Problem

To solve the above-mentioned problems, a method according to an embodiment of the present invention for measuring an amount of a measurement object substance in a sample containing at least a part of blood by utilizing surface plasmon resonance includes: coupling a measurement object substance contained in the sample and a capturing body by supplying the sample onto a metal film of a measurement chip, the measurement chip including a prism having an incidence surface and a film formation surface, the metal film disposed on the film formation surface, and the capturing body fixed on the metal film; irradiating the metal film with excitation light from the prism side in a state where the sample is present on the metal film and measuring a quantity of excitation light reflected by the film formation surface, a resonance angle of the excitation light, a quantity of plasmon scattering light or an enhanced angle of the excitation light to determine whether the sample is whole blood or diluted solution of whole blood with use of an obtained measurement value, and, when the sample is determined to be whole blood or diluted solution of whole blood, acquire a hematocrit value of the whole blood with use of the obtained measurement value; irradiating the metal film with excitation light from the prism side in a state where the measurement object substance and the capturing body are coupled together and the sample is not present on the metal film and measuring a quantity of fluorescence emitted from a vicinity of a surface of the metal film which faces away from the prism or a quantity of excitation light reflected by the film formation surface to acquire a first signal value representing an amount of the measurement object substance in the sample; and, when the sample is determined to be whole blood or diluted solution of whole blood, converting the first signal value to a second signal value representing an amount of the measurement object substance in the liquid component of the sample with use of the hematocrit value of the whole blood.

In addition, to solve the above-mentioned problems, a measurement device according to an embodiment of the present invention is configured to measure an amount of a measurement object substance in a sample containing at least a part of blood by utilizing surface plasmon resonance, the measurement device including: a holder configured to hold a measurement chip including a prism having an incidence surface and a film formation surface, a metal film disposed on the film formation surface, and a capturing body disposed on the metal film; an excitation light irradiation section configured to emit excitation light toward the incidence surface; a light detection section configured to detect a quantity of light emitted from a vicinity of a surface of the metal film which faces away from the prism, or a quantity of excitation light reflected by the film formation surface of the prism; a processing section configured to determine whether the sample is whole blood or diluted solution of whole blood from a detection result of the light detection section, and calculate a first signal value representing an amount of the measurement object substance in the sample from the detection result of the light detection section. When the sample is determined to be whole blood or diluted solution of whole blood, the processing section calculates a hematocrit value of the whole blood from the detection result of the light detection section and converts the first signal value to a second signal value representing an amount of the measurement object substance in the liquid component of the sample with use of the hematocrit value of the whole blood. The processing section determines whether the sample is whole blood or diluted solution of whole blood with use of a quantity of excitation light reflected by the film formation surface and measured by the light detection section, a resonance angle of the excitation light, a quantity of plasmon scattering light or an enhanced angle of the excitation light when the excitation light irradiation section irradiates the metal film with excitation light from the prism side in a state where the sample is present on the metal film; and, when the sample is determined to be whole blood or diluted solution of whole blood, the processing section acquires a hematocrit value of the whole blood with use of the quantity of the excitation light reflected by the film formation surface and measured by the light detection section, the resonance angle of the excitation light, the quantity of the plasmon scattering light or the enhanced angle of the excitation light.

Advantageous Effects of Invention

According to the present invention, in a measurement method and a measurement device which utilize SPR, it is possible to precisely measure the hematocrit value without employing additional devices. According to the present invention, the amount of a measurement object substance in a liquid component of a sample containing at least a part of blood can be measured at low cost, and with high sensitivity and high accuracy.

DESCRIPTION OF EMBODIMENT

In the following, an embodiment of the present invention is described in detail with reference to the accompanying drawings. Here, a surface plasmon-field enhanced fluorescence analysis device (SPFS device) for measuring the amount of a measurement object substance contained in a sample containing at least a part of blood is described as a typical example of the measurement device according to the embodiment of the present invention. Examples of the sample include whole blood (blood which is not subjected to separation or dilution), plasma, serum, and diluted solution thereof.

Figure 1:
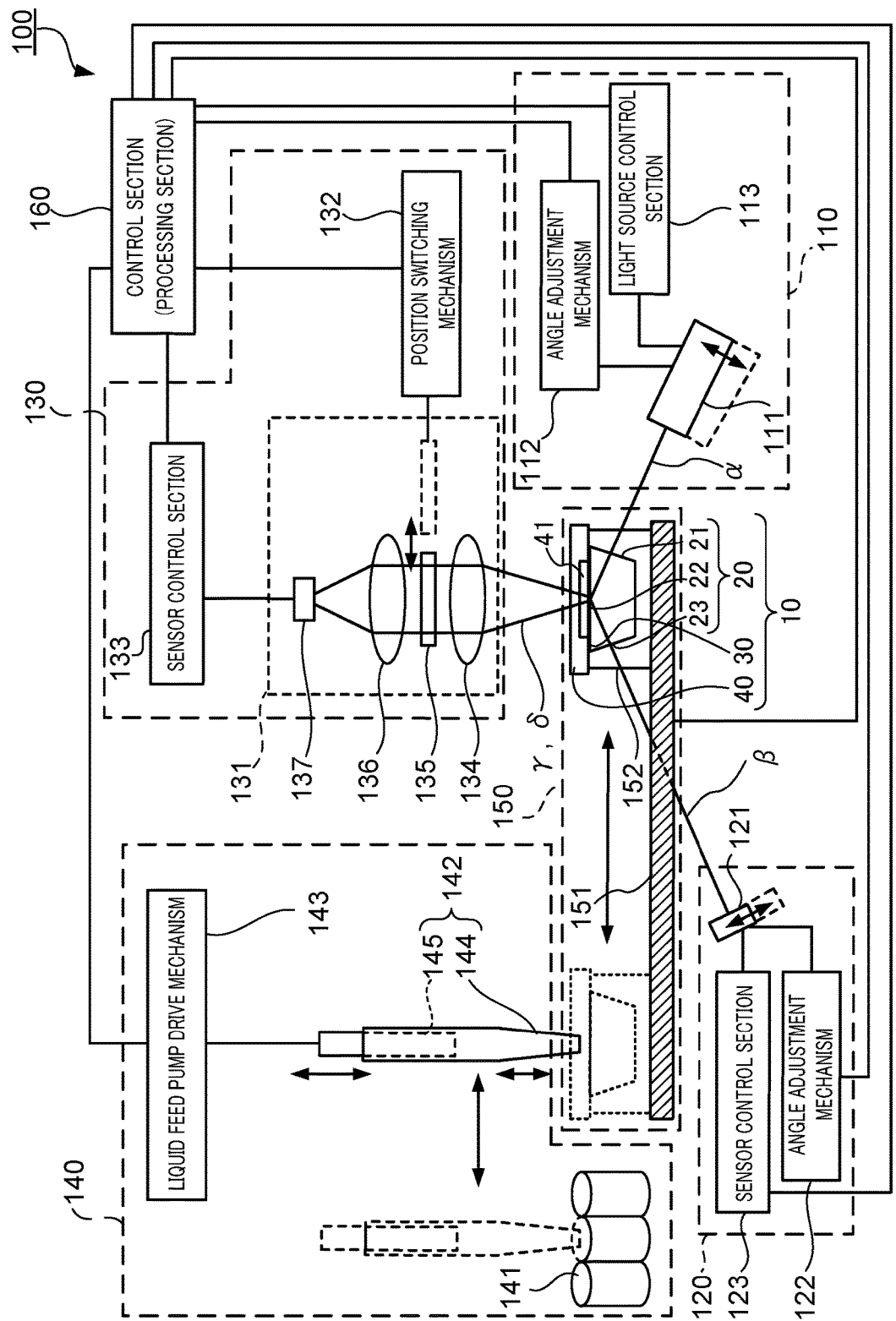
FIG. 1 is a schematic view illustrating a configuration of a surface plasmon-field enhanced fluorescence analysis device according to an embodiment.

FIG. 1 is a schematic view illustrating a configuration of surface plasmon-field enhanced fluorescence analysis device (SPFS device) 100 according to an embodiment of the present invention. As illustrated in FIG. 1, SPFS device 100 includes excitation light irradiation unit 110, reflection light detection unit 120, fluorescence detection unit 130, liquid feed unit 140, conveyance unit 150 and control section 160. SPFS device 100 is used in a state where measurement chip 10 is attached to chip holder 152 of conveyance unit 150. For such a configuration, measurement chip 10 is described first, and then the components of SPFS device 100 are described.

Measurement chip 10 includes prism 20 having incidence surface 21, film formation surface 22 and emission surface 23, metal film 30 formed on film formation surface 22, and channel closure 40 disposed on film formation surface 22 or metal film 30. Normally, measurement chip 10 is replaced for each analysis. Measurement chip 10 is preferably a structure with each side of several millimeters to several centimeters, but may be a smaller or larger structure which is not categorized as "chip."

Prism 20 is a dielectric which is transparent to excitation light α. Prism 20 includes incidence surface 21, film formation surface 22 and emission surface 23. Incidence surface 21 is a surface through which excitation light α from excitation light irradiation unit 110 enters prism 20. Metal film 30 is disposed on film formation surface 22. Excitation light α having entered prism 20 is reflected by the rear surface of metal film 30 and becomes reflection light β. To be more specific, excitation light α is reflected by an interface (film formation surface 22) between prism 20 and metal film 30 and becomes reflection light β. Emission surface 23 emits reflection light β to outside of prism 20.

The shape of prism 20 is not limited. In the present embodiment, the shape of prism 20 is a column whose bottom surface is a trapezoid. The surface corresponding to a bottom side of the trapezoid is film formation surface 22. The surface corresponding to one of the legs is incidence surface 21, and the surface corresponding to the other of the legs is emission surface 23. Preferably, the trapezoid serving as the bottom surface is an isosceles trapezoid. With such a configuration, incidence surface 21 and emission surface 23 are symmetrical, and the S wave component of excitation light α does not easily remain in prism 20.

Incidence surface 21 is formed such that excitation light α does not return to excitation light irradiation unit 110. When excitation light α returns to a laser diode (hereinafter also referred to as "LD") in the case where the light source of excitation light α is the LD, the excitation state of the LD is disturbed, and the wavelength and the output of excitation light α are varied. In view of this, the angle of incidence surface 21 is set within a scanning range around an ideal resonance angle or enhanced angle such that excitation light α is not perpendicularly incident on incidence surface 21. Here, the "resonance angle" is the incident angle at which the quantity of reflection light β emitted from emission surface 23 is minimized when the incident angle of excitation light α with respect to metal film 30 is scanned. In addition, the "enhanced angle" is the incident angle at which the quantity of diffusing light (hereinafter referred to as "plasmon scattering light") β having a wavelength equal to that of excitation light α emitted upward of measurement chip 10 is maximized when the incident angle of excitation light α with respect to metal film 30 is scanned. In the present embodiment, each of the angle between incidence surface 21 and film formation surface 22 and the angle between film formation surface 22 and emission surface 23 is approximately 80 degrees.

It is to be noted that the resonance angle (and the enhanced angle in the close vicinity of the resonance angle) largely depends on the design of measurement chip 10. The design factors are the refractive index of prism 20, the refractive index of metal film 30, the film thickness of metal film 30, the extinction coefficient of metal film 30, the wavelength of excitation light α, and the like. While the resonance angle and the enhanced angle are shifted by a measurement object substance captured on metal film 30, the shift amount is smaller than several degrees.

Prism 20 has a birefringence property to a certain degree. Examples of the material of prism 20 include a resin and glass. Preferably, the material of prism 20 is a resin which has a refractive index of 1.4 to 1.6 and causes a small birefringence.

Metal film 30 is disposed on film formation surface 22 of prism 20. With this configuration, interaction (SPR) is caused between the photon of excitation light α which is incident on film formation surface 22 under the total reflection condition and the free electron in metal film 30, and thus localized-field light (which is also generally called "evanescent light" or "near-field light") can be generated on the surface of metal film 30.

The material of metal film 30 is not limited as long as surface plasmon resonance can be caused. Examples of the material of metal film 30 include gold, silver, copper, aluminum, and their alloys. In the present embodiment, metal film 30 is a thin film formed of gold. The formation method for metal film 30 is not limited. Examples of the formation method for metal film 30 include sputtering, deposition, and plating. Preferably, the thickness of metal film 30 is, but not limited to, 30 to 70 nm.

In addition, although not illustrated in FIG. 1, a capturing body for capturing the measurement object substance is fixed on the surface (front surface of metal film 30) of metal film 30 on the side opposite to prism 20. When a capturing body is fixed, the measurement object substance can be selectively measured. In the present embodiment, a capturing body is uniformly fixed in a predetermined region (reaction site) on metal film 30. The type of the capturing body is not limited as long as the measurement object substance can be captured. In the present embodiment, the capturing body is an antibody specific to the measurement object substance or a fragment of the antibody.

The channel closure 40 is disposed on metal film 30. When metal film 30 is only partly formed on film formation surface 22 of prism 20, channel closure 40 may be disposed on film formation surface 22. A channel groove is formed on the rear surface of channel closure 40, and channel closure 40 forms liquid flow channel 41 together with metal film 30 (and prism 20). Examples of the liquid include a sample containing a measurement object substance (whole blood, plasma, serum or diluted solution thereof), labeling solution containing a capturing body labeled with a fluorescence material, reference solution, washing solution and the like. The capturing body fixed on metal film 30 is exposed to the interior of channel 41. Both ends of channel 41 are respectively connected to the inlet and the outlet which are not illustrated and formed on the top surface of channel closure 40. When liquid is injected into channel 41, the liquid makes contact with the capturing body.

Preferably, channel closure 40 is formed of a material which is transparent to fluorescence γ and plasmon scattering light δ emitted from metal film 30. Examples of the material of channel closure 40 include a resin. As long as the part for taking out fluorescence γ and plasmon scattering light δ is transparent to fluorescence γ and plasmon scattering light δ, other parts of channel closure 40 may be formed of an opaque material. Channel closure 40 is joined to metal film 30 or prism 20 by bonding using a double-sided tape, adhesive agent and the like, laser welding, ultrasound welding, pressure bonding using a clamp member and the like, for example.

As illustrated in FIG. 1, excitation light α enters prism 20 from incidence surface 21. Excitation light α having entered prism 20 is incident on metal film 30 at a total reflection angle (an angle at which SPR is caused). By irradiating metal film 30 with excitation light α at an angle at which SPR is caused, localized light can be generated on metal film 30. With the localized light, the fluorescence material for labelling the measurement object substance placed on metal film 30 is excited, and fluorescence γ is emitted. By measuring the quantity of fluorescence γ emitted from the fluorescence material, SPFS device 100 measures the amount of the measurement object substance.

Next, the components of SPFS device 100 are described. As described above, SPFS device 100 includes excitation light irradiation unit 110, reflection light detection unit 120, fluorescence detection unit 130, liquid feed unit 140, conveyance unit 150 and control section 160.

Excitation light irradiation unit 110 irradiates measurement chip 10 held by chip holder 152 with excitation light α. At the time of measurement of fluorescence γ or plasmon scattering light δ, excitation light irradiation unit 110 emits only P wave with respect to metal film 30 toward incidence surface 21 such that the incident angle to metal film 30 is an angle at which SPR is caused. Here, "excitation light" is light which directly or indirectly excites a fluorescence material. For example, excitation light α is light which generates localized light which excites a fluorescence material on the surface of metal film 30 when it is emitted to metal film 30 through prism 20 at an angle which causes SPR. Excitation light irradiation unit 110 includes light source unit 111, angle adjustment mechanism 112 and light source control section 113.

Light source unit 111 emits collimated excitation light α having a constant wavelength and a constant quantity such that the irradiation spot on the rear surface of metal film 30 has a substantially circular shape. Light source unit 111 includes, for example, a light source of excitation light α, a beam shaping optical system, an APC mechanism and a temperature adjustment mechanism (which are not illustrated).

The type of the light source is not limited, and is a laser diode (LD), for example. Other examples of the light source include a light-emitting diode, a mercury lamp, and other laser light sources. In the case where the light emitted from the light source is not a beam, the light emitted from the light source is converted to a beam by a lens, a mirror, a slit or the like. In addition, in the case where the light emitted from the light source is not monochromatic light, the light emitted from the light source is converted to monochromatic light by a diffraction grid or the like. Further, in the case where the light emitted from the light source is not linear polarization, the light emitted from the light source is converted to light of linear polarization by a polarizer or the like.

The beam shaping optical system includes a collimator, a band pass filter, a linear polarization filter, a half-wave plate, a slit, a zooming unit and the like, for example. The beam shaping optical system may include one or more of the above-mentioned components. The collimator collimates excitation light α emitted from the light source. The band pass filter changes excitation light α emitted from the light source to narrowband light composed only of a central wavelength. The reason for this is that excitation light α from the light source has a slight wavelength distribution width. The linear polarization filter changes excitation light α emitted from the light source to linearly polarized light. The half-wave plate adjusts the polarization direction of excitation light α such that the P wave component is incident on metal film 30. The slit and the zooming unit adjust the beam diameter, the outline shape and the like of excitation light α such that the shape of the irradiation spot on the rear surface of metal film 30 has a circular shape having a predetermined size.

The APC mechanism controls the light source such that the output of the light source is maintained at a constant value. To be more specific, the APC mechanism detects the quantity of the light diverged from excitation light α by a photodiode not illustrated and the like. Then, the APC mechanism controls the input energy by a recurrent circuit to control the output of the light source at a constant value.

The temperature adjustment mechanism is composed of a heater, a Peltier device, or the like, for example. The wavelength and the energy of the light emitted from the light source can be varied by the temperature. Therefore, the temperature of the light source is maintained at a constant value by the temperature adjustment mechanism to control the wavelength and the energy of the light emitted from the light source at a constant value.

Angle adjustment mechanism 112 adjusts the incident angle of excitation light α with respect to metal film 30 (the interface between prism 20 and metal film 30 (film formation surface 22)). Angle adjustment mechanism 112 relatively rotates the optical axis of excitation light α and chip holder 152 to emit excitation light α at a predetermined incident angle toward a predetermined position of metal film 30 through prism 20.

For example, angle adjustment mechanism 112 turns light source unit 111 around an axis orthogonal to the optical axis of excitation light α (an axis in a perpendicular direction as seen in FIG. 1). At this time, the position of the rotation axis is set such that the position of the irradiation spot on metal film 30 is not substantially moved when the incident angle is scanned. By setting the position of the rotation center at a position near the intersection of the optical axes of two rays of excitation light α at both ends of the scanning range of the incident angle (at a position between the irradiation position on film formation surface 22 and incidence surface 21), the shift of the irradiation position can be minimized.

As described above, in the incident angle of excitation light α with respect to metal film 30, the enhanced angle is an angle at which the quantity of plasmon scattering light β is maximized By setting the incident angle of excitation light α to the enhanced angle or an angle approximately equal to the enhanced angle, fluorescence γ having a high intensity can be measured. While the basic incident condition of excitation light α is determined by the material and the shape of prism 20 of measurement chip 10, the film thickness of metal film 30, the refractive index of the liquid in channel 41 and the like, the optimum incident condition is slightly varied depending on the type and the amount of the fluorescence material in channel 41, shaping errors of prism 20 and the like. Therefore, it is preferable to determine an optimum enhanced angle in each measurement.

Light source control section 113 controls components included in light source unit 111 to control emission of excitation light α from light source unit 111. Light source control section 113 is composed of a publicly known computer, microcomputer, or the like including a computation device, a control device, a storage device, and an inputting device, for example.

For the purpose of measurement of the resonance angle, measurement of the hematocrit value of a sample and the like, reflection light detection unit 120 measures the quantity of reflection light β generated by irradiation of measurement chip 10 with excitation light α. Reflection light detection unit 120 includes light receiving sensor 121, angle adjustment mechanism 122 and sensor control section 123.

Light receiving sensor 121 is disposed at a position where reflection light β is incident, and measures the quantity of reflection light β. The type of light receiving sensor 121 is not limited. For example, light receiving sensor 121 is a photodiode (PD).

Angle adjustment mechanism 122 adjusts the position (angle) of light receiving sensor 121 in accordance with the incident angle of excitation light α with respect to metal film 30. Angle adjustment mechanism 122 relatively rotates light receiving sensor 121 and chip holder 152 such that reflection light β is incident on light receiving sensor 121.

Sensor control section 123 controls detection of the output value of light receiving sensor 121, management of the sensitivity of light receiving sensor 121 according to the detected output value, change of the sensitivity of light receiving sensor 121 for obtaining an appropriate output value, and the like. Sensor control section 123 is composed of a publicly known computer, microcomputer, or the like including a computation device, a control device, a storage device, and an inputting device, for example.

Fluorescence detection unit 130 detects fluorescence γ generated by irradiation of metal film 30 with excitation light α. In addition, as necessary, fluorescence detection unit 130 also detects plasmon scattering light δ generated by irradiation of metal film 30 with excitation light α. Fluorescence detection unit 130 includes light reception unit 131, position switching mechanism 132 and sensor control section 133.

Light reception unit 131 is disposed in the direction of the normal of metal film 30 of measurement chip 10. Light reception unit 131 includes first lens 134, optical filter 135, second lens 136 and light receiving sensor 137.

First lens 134 is, for example, a condenser lens, and condenses the light emitted from metal film 30. Second lens 136 is, for example, an image forming lens, and images the light condensed by first lens 134 on the light reception surface of light receiving sensor 137. The light paths between the lenses are substantially parallel to each other. Optical filter 135 is disposed between the lenses.

Optical filter 135 guides only the fluorescence component to light receiving sensor 137, and removes the excitation light component (plasmon scattering light δ) in order to detect fluorescence γ with a high S/N ratio. Examples of optical filter 135 include an excitation light reflection filter, a short wavelength cut filter and a band pass filter. Optical filter 135 is, for example, a filter including a multi-layer film that reflects a predetermined light component, or a color glass filter that absorbs a predetermined light component.

Light receiving sensor 137 detects fluorescence γ and plasmon scattering light δ. Light receiving sensor 137 has a high sensitivity such that weak fluorescence γ from a very small amount of the measurement object substance can be detected. Light receiving sensor 127 is, for example, a photomultiplier tube (PMT), an avalanche photodiode (APD) or the like.

Position switching mechanism 132 switches the position of optical filter 135 between a position on the light path and a position outside the light path in light reception unit 131. To be more specific, optical filter 135 is disposed on the light path of light reception unit 131 when light receiving sensor 137 detects fluorescence γ, and optical filter 135 is disposed at a position outside the light path of light reception unit 131 when light receiving sensor 137 detects plasmon scattering light δ.

Sensor control section 133 controls detection of the output value of light receiving sensor 137, management of the sensitivity of light receiving sensor 137 according to the detected output value, change of the sensitivity of light receiving sensor 137 for obtaining an appropriate output value and the like. Sensor control section 133 is composed of a publicly known computer, microcomputer, or the like including a computation device, a control device, a storage device, and an inputting device, for example.

Liquid feed unit 140 supplies a sample, labeling solution, reference solution, washing solution and the like into channel 41 of measurement chip 10 held by chip holder 152. Liquid feed unit 140 includes liquid chip 141, syringe pump 142 and liquid feed pump drive mechanism 143.

Liquid chip 141 is a container for housing a sample and liquid such as labeling solution, reference solution, washing solution. Normally, as liquid chip 141, a plurality of containers corresponding to the types of the liquid are disposed, or a chip composed of a plurality of integrated containers is disposed.

Syringe pump 142 is composed of syringe 144, and plunger 145 which can reciprocate in syringe 144. Through reciprocation of plunger 145, suction and ejection of the liquid is quantitatively performed. When syringe 144 is replaceable, washing of syringe 144 is unnecessary. Such a configuration is preferable from the viewpoint of preventing entrance of impurities. When syringe 144 is not replaceable, it is possible to use syringe 144 without replacing syringe 144 by additionally providing a configuration for washing the interior of syringe 144.

Liquid feed pump drive mechanism 143 includes a driving device of plunger 145, and a moving device of syringe pump 142. The driving device of syringe pump 142 is a device for reciprocating plunger 145, and includes a stepping motor, for example. The driving device including a stepping motor can manage the liquid feed amount and the liquid feed speed of syringe pump 142, and is therefore preferable from the viewpoint of managing the amount of the residual liquid of measurement chip 10. The moving device of syringe pump 142 freely moves syringe pump 142 in the axial direction (for example, a vertical direction) of syringe 144 and a direction (for example, a horizontal direction) crossing the axial direction, for example. The moving device of syringe pump 142 is composed of a robot arm, a biaxial stage or a vertically movable turntable, for example.

Liquid feed unit 140 sucks various kinds of liquid from liquid chip 141, and supplies the liquid into channel 41 of measurement chip 10. At this time, when plunger 145 is moved, the liquid reciprocates in channel 41 in measurement chip 10, and the liquid in channel 41 is agitated. In this manner, uniformization of the density of the liquid, facilitation of reaction (for example, antigen-antibody reaction) in channel 41 and the like can be achieved. From the view point of performing the above-mentioned operations, it is preferable that measurement chip 10 and syringe 144 be configured such that the inlet of measurement chip 10 is protected with a multi-layer film and that the inlet can be sealed when syringe 144 penetrates the multi-layer film.

The liquid in channel 41 is again sucked by syringe pump 142, and ejected to liquid chip 141 and the like. By repeating the above-mentioned operations, reaction, washing and the like of various kinds of liquid can be performed, and a measurement object substance labeled by a fluorescence material can be placed at a reaction site in channel 41.

Conveyance unit 150 conveys measurement chip 10 to a measurement position or a liquid feeding position, and fixes measurement chip 10. Here, the "measurement position" is a position where excitation light irradiation unit 110 irradiates measurement chip 10 with excitation light α, and where reflection light detection unit 120 or fluorescence detection unit 130 detects the reflection light β, fluorescence γ or plasmon scattering light δ generated by the irradiation. In addition, the "liquid feeding position" is a position where liquid feed unit 140 supplies liquid into channel 41 of measurement chip 10, or removes the liquid in channel 41 of measurement chip 10. Conveyance unit 150 includes conveyance stage 151 and chip holder 152. Chip holder 152 is fixed to conveyance stage 151 and detachably holds measurement chip 10. Chip holder 152 has a shape which can hold measurement chip 10 and does not block the light paths of excitation light α, reflection light β, fluorescence γ and plasmon scattering light δ. For example, chip holder 152 is provided with an opening through which excitation light α, reflection light β, fluorescence γ and plasmon scattering light δ pass. Conveyance stage 151 moves chip holder 152 in two opposite directions. Conveyance stage 151 also has a shape which does not block the light paths of excitation light α, reflection light β, fluorescence γ and plasmon scattering light δ. Conveyance stage 151 is driven by a stepping motor and the like, for example.

Control section 160 controls angle adjustment mechanism 112, light source control section 113, angle adjustment mechanism 122, sensor control section 123, position switching mechanism 132, sensor control section 133, liquid feed pump drive mechanism 143 and conveyance stage 151. In addition, control section 160 also functions as a processing section which determines whether the sample is a sample containing whole blood, that is, whether or not the sample is whole blood or diluted solution of whole blood on the basis of a detection result of reflection light detection unit 120 and/or fluorescence detection unit 130. Further, control section 160 also functions as a processing section which calculates the hematocrit value of the whole blood contained in the sample on the basis of the detection result of reflection light detection unit 120 and/or fluorescence detection unit 130 when it is determined that the sample is whole blood or diluted solution of whole blood. Control section 160 is composed of a publicly known computer, microcomputer, or the like including a computation device, a control device, a storage device, and an inputting device, for example.

Figure 2:
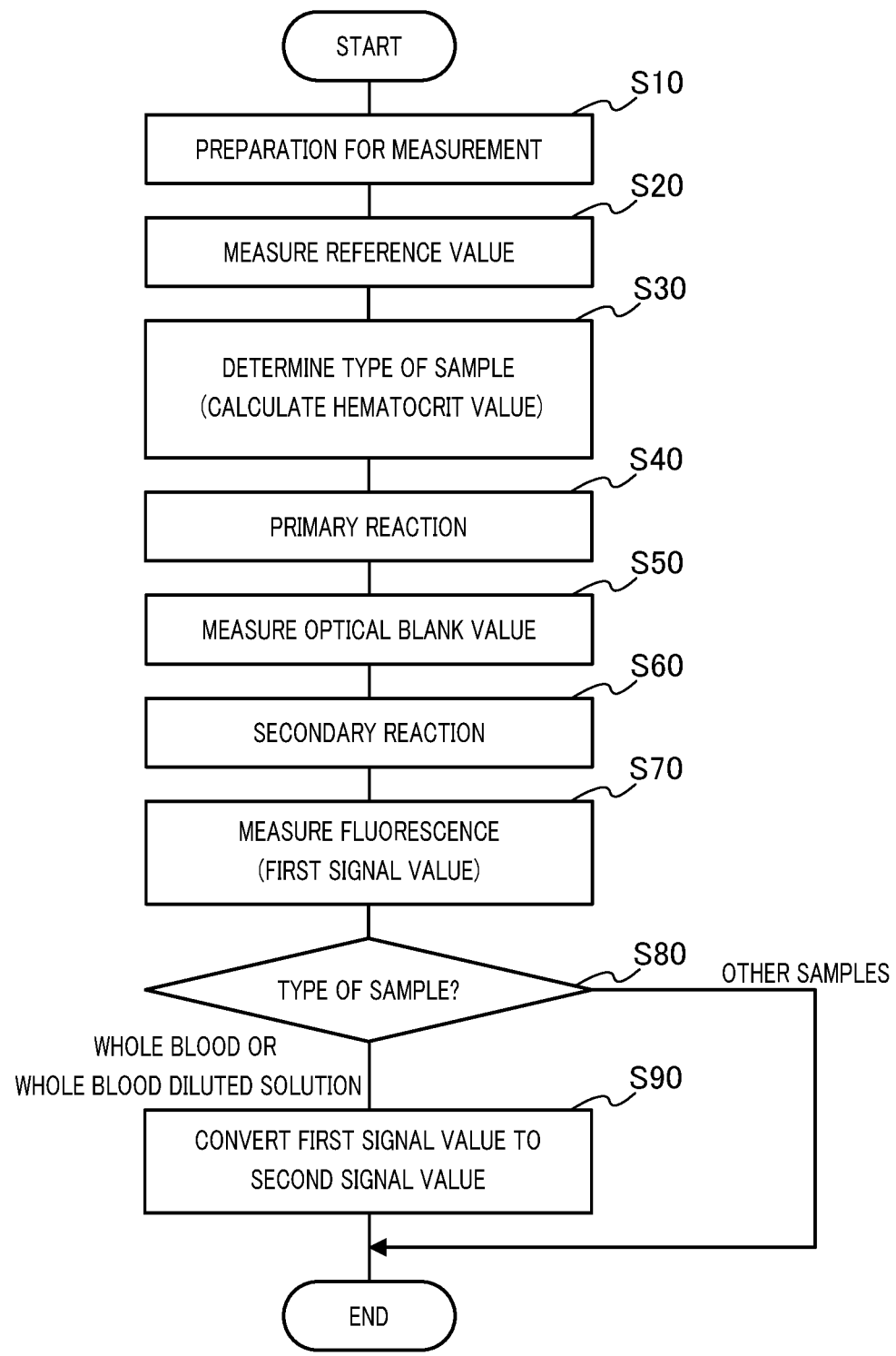
FIG. 2 is a flowchart of an exemplary operation procedure of the device illustrated in FIG. 1.

Next, a detection operation of SPFS device 100 (the measurement method according to the embodiment of the present invention) is described. FIG. 2 is a flowchart of an exemplary operation procedure of SPFS device 100.

First, preparation for measurement is performed (step S10). To be more specific, measurement chip 10 is placed at chip holder 152 of SPFS device 100. When moisturizing agent is present in channel 41 of measurement chip 10, the interior of channel 41 is washed to remove the moisturizing agent so that the capturing body can appropriately capture the measurement object substance.

Next, a reference value which is used in a later step (step S30) is measured (step S20). To be more specific, control section 160 operates conveyance stage 151 to move measurement chip 10 to a liquid feeding position. Thereafter, control section 160 operates liquid feed unit 140 to introduce the reference solution in liquid chip 141 into channel 41 of measurement chip 10. The reference solution is, for example, a buffer solution such as phosphate buffered physiological saline (PBS), tris-buffered physiological saline (TBS) and HEPES-buffered physiological saline (HBS). Next, control section 160 operates conveyance stage 151 to move measurement chip 10 to a measurement position. Thereafter, control section 160 operates excitation light irradiation unit 110, reflection light detection unit 120 or fluorescence detection unit 130 to measure a reference value for measuring the hematocrit value. The reference value measured herein is one or more parameter values selected from a group consisting of the quantity of reflection light $\beta$, the resonance angle of excitation light $\alpha$, the quantity of plasmon scattering light $\delta$ and the enhanced angle of excitation light $\alpha$, which are identical to the parameter values measured in the later step S30. Here, the "quantity of reflection light $\beta$" refers to the minimum value of the quantity of reflection light $\beta$ emitted from the emission surface 23 of measurement chip 10 when the incident angle of excitation light is scanned. In addition, the "quantity of plasmon scattering light $\delta$" refers to the quantity of plasmon scattering light $\delta$ emitted upward of measurement chip 10 when the metal film is irradiated with excitation light $\alpha$ at a specific incident angle (normally, an enhanced angle).

For example, when measuring the quantity of reflection light $\beta$ or the resonance angle of excitation light $\alpha$, control section 160 operates excitation light irradiation unit 110 to scan the incident angle of excitation light $\alpha$ with respect to metal film 30, while operating reflection light detection unit 120 to measure the quantity of reflection light $\beta$. When measuring the quantity of plasmon scattering light $\delta$, control section 160 operates excitation light irradiation unit 110 to emit excitation light $\alpha$ at a predetermined incident angle, while operating fluorescence detection unit 130 to measure the quantity of plasmon scattering light $\delta$. When measuring the enhanced angle of excitation light $\alpha$, control section 160 operates excitation light irradiation unit 110 to scan the incident angle of excitation light $\alpha$ to metal film 30, while operating fluorescence detection unit 130 to measure the quantity of plasmon scattering light $\delta$. The measured reference value is recorded in control section 160.

Next, it is determined whether the sample is a sample which contains whole blood (for example, whole blood or diluted solution of whole blood), or not (for example, plasma, serum or diluted solution thereof). In addition, when the sample is a sample which contains whole blood, the hematocrit value of the whole blood contained in the sample is measured (step S30). In addition, by performing this step, the measurement object substance is captured on metal film 30 by antigen-antibody reaction in channel 41 (primary reaction; step S40). It is to be noted that primary reaction (step S40) may be performed before determination of the type of the sample (step S30).

To be more specific, control section 160 operates conveyance stage 151 to move measurement chip 10 to a liquid feeding position (step S110). Thereafter, control section 160 operates liquid feed unit 140 to remove the reference solution in channel 41 of measurement chip 10, and introduce the sample in liquid chip 141 into channel 41. In channel 41, by antigen-antibody reaction, the measurement object substance is captured on metal film 30 (primary reaction). Next, control section 160 operates conveyance stage 151 to move measurement chip 10 to a measurement position. Thereafter, control section 160 operates excitation light irradiation unit 110, reflection light detection unit 120 or fluorescence detection unit 130 to measure the quantity of reflection light $\beta$, the resonance angle of excitation light $\alpha$, the quantity of plasmon scattering light $\delta$ or the enhanced angle of excitation light $\alpha$. The procedure of measurement of the quantity of reflection light $\beta$, the resonance angle of excitation light $\alpha$, the quantity of plasmon scattering light $\delta$ and the enhanced angle of excitation light $\alpha$ is identical to that of the measurement of the reference value (step S20). The measurement value is recorded in control section 160.

Thereafter, control section 160 subtracts the reference value obtained in step S20 from the measurement value, and calculates a change value ($\Delta$ reflection light quantity, $\Delta$ resonance angle, $\Delta$ plasmon scattering light quantity or $\Delta$ enhanced angle) which indicates whether the sample contains a blood cell component. Next, using the change value as an index, control section 160 determines whether the sample is a sample which contains whole blood (for example, whole blood or diluted solution of whole blood) or not (for example, plasma, serum or diluted solution thereof). The determination result is recorded in control section 160.

When the sample is a sample which contains whole blood, control section 160 further calculates the hematocrit value of the whole blood contained in the sample with use of the above-described change value ($\Delta$ reflection light quantity, $\Delta$ resonance angle, $\Delta$ plasmon scattering light quantity or $\Delta$ enhanced angle) as an index. Since the above-described change value corresponds to the hematocrit value of the whole blood contained in the sample, control section 160 uses the above-described change value with a calibration curve prepared in advance to calculate the hematocrit value of the whole blood contained in the sample.

Figure 4A:
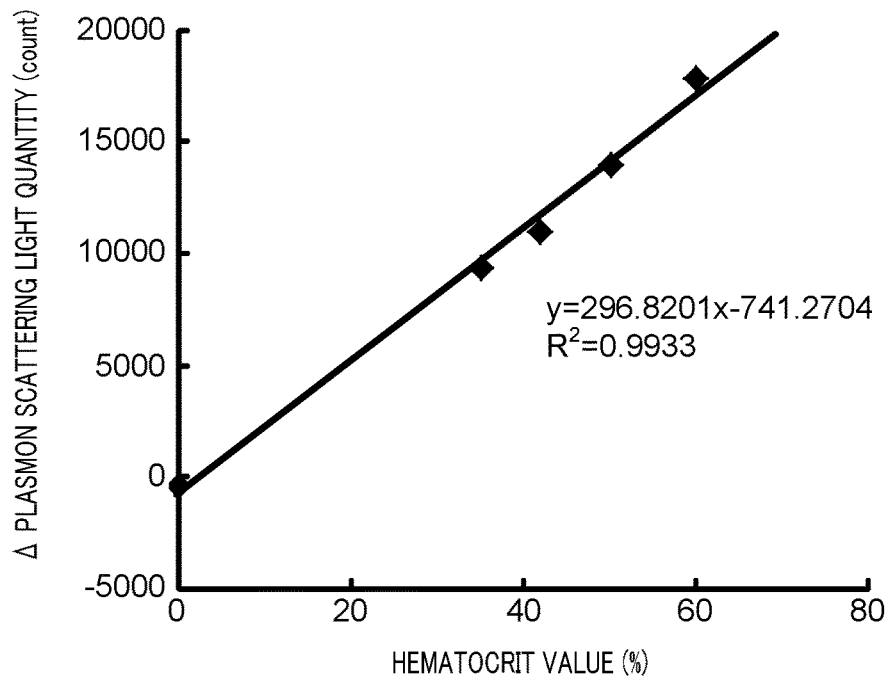
FIGS. 4A and 4B are graphs showing a calibration curve.
Figure 4B:
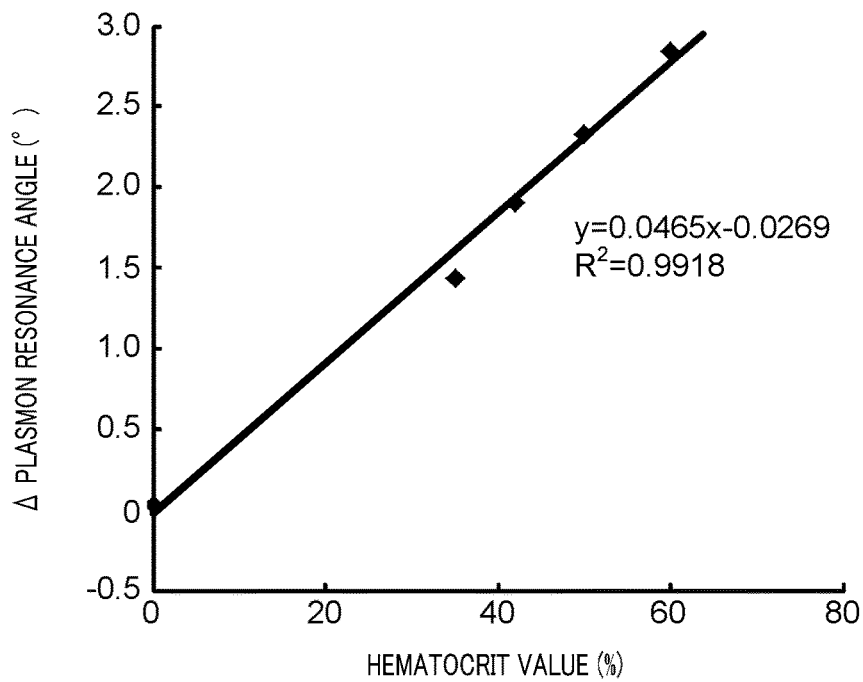

The calibration curve is a graph which shows the relationship between a hematocrit value of whole blood and the above-mentioned change value ($\Delta$ reflection light quantity, $\Delta$ resonance angle, $\Delta$ plasmon scattering light quantity or $\Delta$ enhanced angle). FIG. 4A is a graph (calibration curve) illustrating an exemplary relationship between the hematocrit value of whole blood and the $\Delta$ plasmon scattering light quantity, and FIG. 4B is a graph (calibration curve) illustrating an exemplary relationship between the hematocrit value of whole blood and the $\Delta$ resonance angle. When the same measurement chip 10 and SPFS device 100 are used, the same calibration curve can be used, and, for example, the calibration curve is recorded in control section 160.

Next, an optical blank value is measured (step S50). Here, the "optical blank value" refers to the quantity of background light emitted upward of measurement chip 10 in measurement of fluorescence γ (step S70). To be more specific, control section 160 operates conveyance stage 151 to move measurement chip 10 to a liquid feeding position. Thereafter, control section 160 operates liquid feed unit 140 to remove the sample in channel 41 of measurement chip 10, and washes the interior of channel 41 with use of the washing solution in liquid chip 141. Next, control section 160 operates conveyance stage 151 to move measurement chip 10 to a measurement position. Thereafter, control section 160 operates excitation light irradiation unit 110 and fluorescence detection unit 130 to irradiate metal film 30 with excitation light α, and records an output value (optical blank value) of light receiving sensor 137. At this time, control section 160 operates angle adjustment mechanism 112 to set the incident angle of excitation light α to the enhanced angle. In addition, control section 160 controls position switching mechanism 132 to dispose optical filter 135 at a position on the light path of light reception unit 131. The measured optical blank value is recorded in control section 160.

Next, the measurement object substance captured on metal film 30 is labelled with a fluorescence material (secondary reaction; step S60). To be more specific, control section 160 operates conveyance stage 151 to move measurement chip 10 to a liquid feeding position. Thereafter, control section 160 operates liquid feed unit 140 to introduce the liquid (labeling solution) containing the capturing body labeled with the fluorescence material into channel 41 of measurement chip 10. In channel 41, by antigen-antibody reaction, the measurement object substance captured on metal film 30 is labeled with the fluorescence material. Thereafter, the labeling solution in channel 41 is removed, and the interior of the channel is washed with the washing solution.

Next, the quantity of fluorescence β is measured, and a first signal value which represents the amount of a measurement object substance in the sample is obtained (step S70). To be more specific, control section 160 operates conveyance stage 151 to move measurement chip 10 to a measurement position. Thereafter, control section 160 operates excitation light irradiation unit 110 and fluorescence detection unit 130 to irradiate metal film 30 with excitation light α, and records the output value of light receiving sensor 137. At this time, control section 160 operates angle adjustment mechanism 112 to set the incident angle of excitation light α to the enhanced angle. In addition, control section 160 controls position switching mechanism 132 to dispose optical filter 135 at a position on the light path of light reception unit 131. Control section 160 subtracts the optical blank value from the detection value and the first signal value indicating the amount of the measurement object substance in the sample. The first signal value is converted into the amount, the concentration or the like of the measurement object substance as necessary. The first signal value is recorded in control section 160.

Next, it is determined whether the sample is a sample which contains whole blood (for example, whole blood or diluted solution of whole blood), or not (for example, plasma, serum or diluted solution thereof) (step S80). In this step, the determination result of step S30 may be used as it is. When the sample is a sample which contains whole blood (for example, whole blood or diluted solution of whole blood), the process is advanced to a step of converting the signal value with use of the hematocrit value (step S90). When the sample is not a sample which contains whole blood (for example, plasma, serum or diluted solution thereof), conversion of the signal value with use of the hematocrit value is unnecessary, and therefore the detection operation is terminated.

When the sample is a sample which contains whole blood, the first signal value measured in step S70 is converted into the second signal value which represents the amount of the measurement object substance in the liquid component of the sample with use of the hematocrit value of the whole blood measured in step S30 (step S90). To be more specific, when the sample is whole blood which is not diluted, the first signal value is converted to the second signal value by multiplying the first signal value by conversion coefficient $c_1$ expressed by the following expression (1). When the sample is diluted solution of whole blood, the first signal value is converted to the second signal value by multiplying the first signal value by conversion coefficient $c_2$ expressed by the following expression (2). At this time, the first signal value and the second signal value may be a quantity of fluorescence β, or a conversion value such as an amount or a concentration of a measurement object substance.

[Expression 1]

$$c_1 = \frac{1}{\left(1 - \frac{Ht}{100}\right)} \quad (1)$$

[Expression 2]

$$c_2 = \frac{(df - 1) + \left(1 - \frac{Ht}{100}\right)}{df\left(1 - \frac{Ht}{100}\right)} \quad (2)$$

[In Expressions (1) and (2), Ht is a hematocrit value, and df is a dilution ratio of diluted solution]

Through the above-mentioned procedures, the amount of a measurement object substance in the liquid component of the sample can be measured.

In the above-mentioned description, measurement of the quantity of reflection light β, the resonance angle of excitation light α, the quantity of plasmon scattering light δ or the enhanced angle of excitation light α in a state where a sample is introduced (step S30) was performed after the measurement of the reference value (step S20). Alternatively, measurement of the quantity of reflection light β, the resonance angle of excitation light α, the quantity of plasmon scattering light δ or the enhanced angle of excitation light α in a state where a sample is introduced (step S30) may be performed before the measurement of the reference value (step S20). In addition, measurement of the reference value (step S20) may be performed after primary reaction (step S40) or measurement of the optical blank value (step S50). In addition, measurement of the optical blank value (step S50) may be performed after measurement of the reference value (step S20).

In addition, determination of the type of the sample and calculation of the hematocrit value may be performed using the measurement value of the quantity of reflection light β, the resonance angle of excitation light α, the quantity of plasmon scattering light δ or the enhanced angle of excitation light α as it is without using reference value (step S30). In this case, the measurement of the reference value (step S20) is unnecessary.

While a measurement method and a measurement device which use a SPFS are described in the above-mentioned embodiment, the measurement method and the measurement device according to the embodiment of the present invention are not limited to the measurement method and the measurement device which use a SPFS. For example, the measurement method and the measurement device according to the embodiment of the present invention may be a measurement method and a measurement device which use a SPR method. In this case, measurement device 100 measures the quantity of reflection light β as the first signal value without measuring the quantity of fluorescence γ to thereby measure the measurement object substance. Accordingly, measurement of the optical blank value (step S50) and secondary reaction (step S60) are unnecessary.

[Example]

Hereinafter, the present invention is described in detail with reference to Examples, but the present invention is not limited to Examples.

1. Comparison Between Measurement Value of Whole Blood and Measurement Value of Plasma First, with use of SPFS device 100 illustrated in FIG. 1, the concentration of cardiac troponin I in diluted solution of whole blood and diluted solution of plasma was measured. As a sample, tripled diluted solutions of whole blood (A to F) collected from six examinees, and tripled diluted solutions of plasma (A to F) obtained by centrifuging each of the whole blood (1600 g, for 15 minutes) were prepared. A reference solution (a tris buffer solution containing surfactant) described later was used for dilution of the sample. Antimyocardial-troponin I antibody was fixed on a gold thin film (metal film 30) having a film thickness of approximately 40 nm, and a reaction site was formed. The sample is supplied into channel 41, and reaction between the cardiac troponin I in the sample and the fixed antibody was sufficiently caused, and then, washing was performed. Antimyocardial-troponin I antibody containing solution (labeling solution) labeled with a fluorescent dye (Hylyte Fluor 647) was supplied, and reaction between the captured cardiac troponin I and the label antibody was sufficiently caused, and then washing was again performed. Thereafter, the quantity of fluorescence γ of the case where the incident angle of excitation light α (wavelength 650 nm) is the enhanced angle was measured. It is to be noted that the type of the fluorescent dye for labelling the antibody is not limited to the above-mentioned example, and publicly known fluorescent dye may be appropriately selected as long as the fluorescence is not extinguished completely due to the absorbance by metal film 30.

Figure 3:
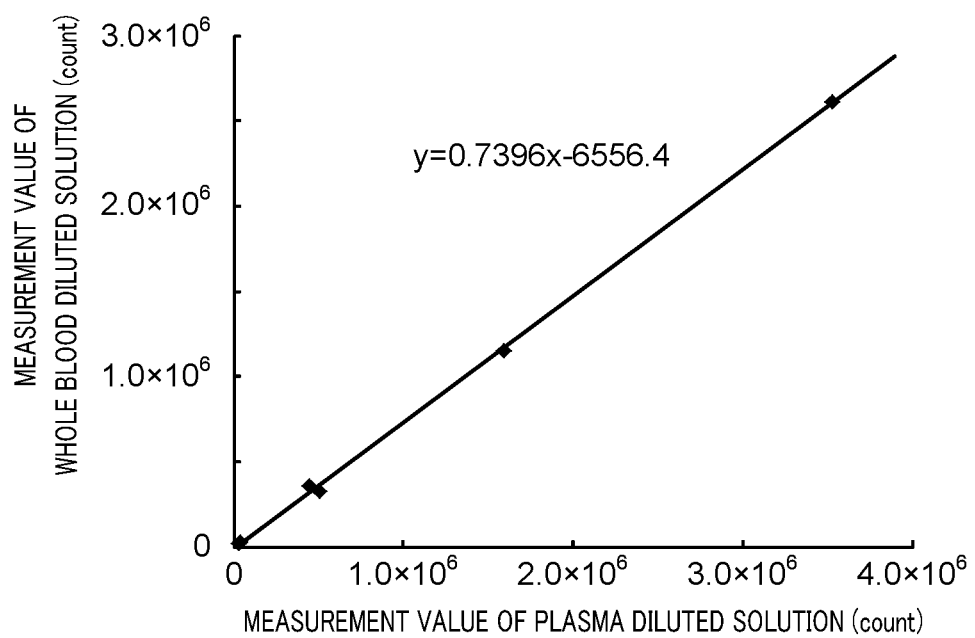
FIG. 3 is a graph showing a relationship between a measurement value of plasma diluted solution and a measurement value of whole blood diluted solution.

The quantity of measured fluorescence γ of each sample is shown in table 1. In addition, FIG. 3 is a graph showing a relationship between the measurement value of the plasma diluted solution and the measurement value of whole blood diluted solution of each examinee (sample). In this graph, when an approximation straight line of the plots was drawn, the inclination of the approximation straight line was 0.7396. In view of this, it can be said that the measurement value of the whole blood diluted solution and the measurement value of the plasma diluted solution are quite different from each other. In addition, the plots are shifted from the approximation straight line, and therefore it can be said that the measurement value of the whole blood diluted solution cannot be accurately converted into the measurement value of the plasma diluted solution by uniformly multiplying the measurement value of the whole blood diluted solution by a conversion coefficient, that is, the conversion coefficient is different among the examinees (samples).

TABLE 1

| Sample | Measurement value of whole blood diluted solution (count) | Measurement value of plasma diluted solution (count) |
| --- | --- | --- |
| A | 26832 | 37657 |
| B | 2610557 | 3528290 |
| C | 18840 | 26741 |
| D | 1153857 | 1588583 |
| E | 325855 | 505370 |
| F | 360751 | 446591 |

2. Preparation of Calibration Curve

Whole bloods whose hematocrit values are known were diluted or concentrated to prepare four different test solutions whose hematocrit values are different from each other. In addition, as blood having a hematocrit value of 0%, plasma was prepared. In addition, as reference solution, tris buffer solution (of pH7.4, containing 0.05% of P20) was also prepared.

With use of SPFS device 100 illustrated in FIG. 1, the plasmon scattering light quantity and the plasmon resonance angle were measured in the state where the tripled diluted solutions of the samples (reference solution, plasma and test solutions 1 to 4) are introduced in channel 41. Table 2 shows a relationship of the hematocrit value of the samples, the plasmon scattering light quantity and the Δ plasmon scattering light quantity of the diluted solutions of the samples (the difference between the plasmon scattering light quantity in the state where the diluted solution of the sample is introduced and the plasmon scattering light quantity in the state where the reference solution is introduced). In addition, table 3 shows a relationship of the hematocrit value of the samples, the plasmon resonance angle and the Δ plasmon resonance angle of the diluted solutions of the samples (the difference between the plasmon resonance angle in the state where the diluted solution of the sample is introduced and the plasmon resonance angle in the state where the reference solution is introduced). While the quantity of the plasmon scattering light in table 2 was measured at the enhanced angle of the diluted solutions of the samples, the incident angle for measurement of the plasmon scattering light quantity may not be the enhanced angle as long as the incident angle is a unified incident angle.

TABLE 2

| Sample | Hematocrit value of sample (%) | Plasmon scattering light quantity of diluted solution (count) | Δ Plasmon scattering light quantity of diluted solution (count) |
| --- | --- | --- | --- |
| Reference solution | — | 68794 | 0 |
| Plasma | 0 | 68388 | −406 |
| Test solution 1 | 35 | 78200 | 9406 |
| Test solution 2 | 42 | 79794 | 11000 |
| Test solution 3 | 50 | 82791 | 13997 |
| Test solution 4 | 60 | 86596 | 17802 |

TABLE 3

| Sample | Hematocrit value of sample (%) | Δ Plasmon resonance angle of diluted solution (°) | Δ Plasmon resonance angle of diluted solution (°) |
| --- | --- | --- | --- |
| Reference solution | — | 67.61 | 0.00 |
| Plasma | 0 | 67.57 | 0.04 |
| Test solution 1 | 35 | 66.17 | 1.44 |
| Test solution 2 | 42 | 65.70 | 1.91 |
| Test solution 3 | 50 | 65.28 | 2.33 |
| Test solution 4 | 60 | 64.76 | 2.85 |

FIG. 4A is a graph showing a calibration curve created from the hematocrit values of the samples shown in table 2 and the quantity of Δ plasmon scattering light of the corresponding diluted solutions of the samples. The $R^2$ value of this calibration curve (approximation straight line) was 0.9933. In addition, FIG. 4B is a graph showing a calibration curve created from the hematocrit values of the samples shown in table 3 and Δ plasmon resonance angles of the corresponding diluted solutions of the samples. The $R^2$ value of this calibration curve (quadratic approximation curve) was 0.9918.

3. Calculation of Hematocrit Value Using Calibration Curve

With use of SPFS device 100 illustrated in FIG. 1, the plasmon scattering light quantity and the plasmon resonance angle in the state where the diluted solution or the reference solution of the whole blood (A to F) is introduced were measured, and Δ plasmon scattering light quantity and Δ plasmon resonance angle were obtained for each whole blood. Next, with use of the calibration curve shown in FIG. 4A, the hematocrit values of the original whole blood were calculated from the quantity of Δ plasmon scattering light of the whole blood diluted solutions. In addition, with use of the calibration curve shown in FIG. 4B, the hematocrit values of the original whole blood were calculated from the Δ plasmon resonance angles of the blood diluted solutions. Table 4 shows the hematocrit values of the whole bloods calculated from the Δ plasmon scattering light quantity. In addition, table 5 shows the hematocrit values of the whole bloods calculated from the Δ plasmon resonance angle.

TABLE 4

| Sample | Δ Plasmon scattering light quantity(count) | Calculated hematocrit value of whole blood (%) |
| --- | --- | --- |
| A | 12556 | 44.8 |
| B | 11458 | 41.1 |
| C | 13358 | 47.5 |
| D | 11963 | 42.8 |
| E | 13150 | 46.8 |
| F | 11161 | 40.1 |

TABLE 5

| Sample | Δ Plasmon resonance angle (°) | Calculated hematocrit value of whole blood (%) |
| --- | --- | --- |
| A | 1.954 | 42.6 |
| B | 1.768 | 38.6 |
| C | 2.061 | 44.9 |

TABLE 5-continued

| Sample | Δ Plasmon resonance angle (°) | Calculated hematocrit value of whole blood (%) |
| --- | --- | --- |
| D | 1.856 | 40.5 |
| E | 2.061 | 44.9 |
| F | 1.768 | 38.6 |

4. Conversion of Measurement Value Using Calculated Hematocrit Value

Conversion coefficient $C_2$ of each whole blood diluted solution was calculated with use of the hematocrit values (the hematocrit values calculated from the Δ plasmon scattering light quantity) shown in table 4, and Expression (2). With use of the obtained conversion coefficient $C_2$, the measurement value of the whole blood diluted solution shown in table 1 was converted to the measurement value of the plasma diluted solution. Table 6 shows the conversion coefficients of the whole blood diluted solutions and the measurement values of the whole blood diluted solutions after conversion.

TABLE 6

| Sample | Measurement value of whole blood diluted solution (count) | Conversion coefficient | Measurement value after conversion (count) |
| --- | --- | --- | --- |
| A | 26832 | 1.41 | 37720 |
| B | 2610557 | 1.35 | 3521372 |
| C | 18840 | 1.45 | 27362 |
| D | 1153857 | 1.37 | 1585544 |
| E | 325855 | 1.44 | 469183 |
| F | 360751 | 1.33 | 481503 |

Figure 5A:
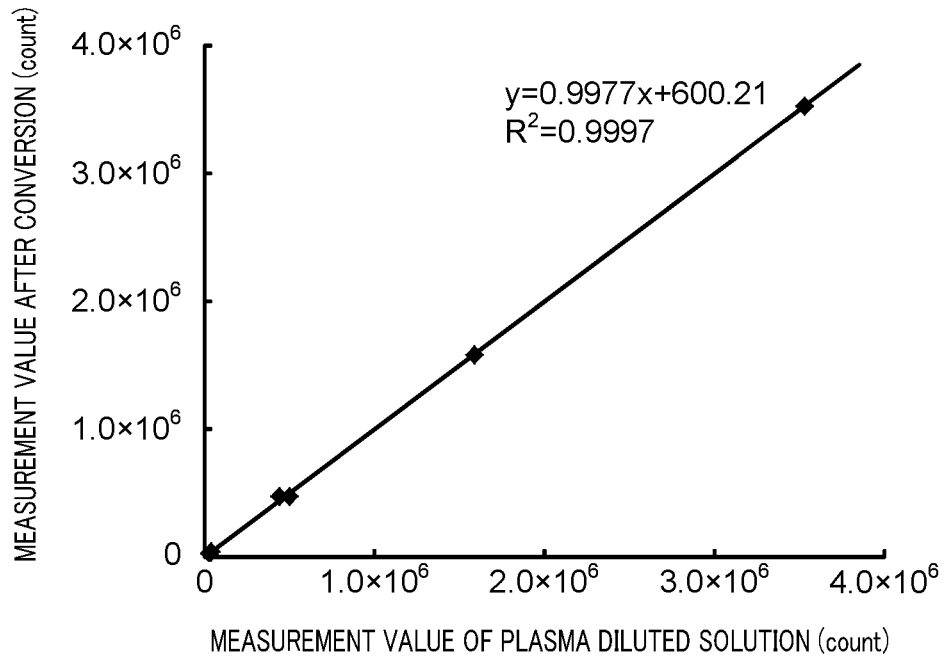
FIGS. 5A and 5B are graphs showing a relationship between a measurement value of plasma diluted solution and a measurement value converted from a measurement value of whole blood diluted solution.

FIG. 5A is a graph showing a relationship between the measurement values of the plasma diluted solution (see table 1) and the measurement values converted from the measurement values of the whole blood diluted solution (see table 6) of the examinees (samples). In this graph, when an approximation straight line (solid line) of the plots was drawn, the approximation straight line had an inclination of 0.9977, and a quite small intercept. In view of this, it can be said that the measurement value of the plasma diluted solution and the measurement value of the whole blood diluted solution after conversion are substantially equal to each other. In addition, it can be said that the conversion coefficient is different among the examinees (samples).

Likewise, conversion coefficient $C_2$ of each whole blood diluted solution was calculated with use of the hematocrit value (the hematocrit value calculated from Δ plasmon resonance angle) shown in table 5 and Expression (2). With use of the obtained conversion coefficients, the measurement values of the whole blood diluted solutions shown in table 1 were converted to the measurement values of the plasma diluted solutions. Table 7 shows the conversion coefficients of the whole blood diluted solutions and the measurement values of the whole blood diluted solutions after conversion.

TABLE 7

| Sample | Measurement value of whole blood diluted solution (count) | Conversion coefficient | Measurement value after conversion (count) |
| --- | --- | --- | --- |
| A | 26832 | 1.37 | 36789 |
| B | 2610557 | 1.31 | 3431140 |
| C | 18840 | 1.41 | 26516 |
| D | 1153857 | 1.34 | 1546556 |
| E | 325855 | 1.41 | 458622 |
| F | 360751 | 1.31 | 474146 |

Figure 5B:
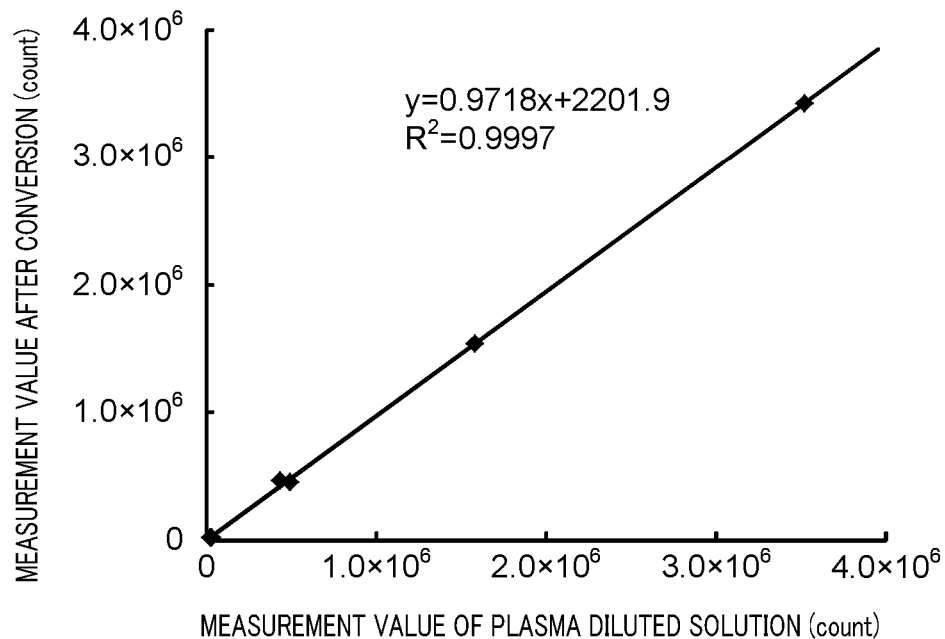

FIG. 5B is a graph showing a relationship between the measurement values of the plasma diluted solution (see table 1) and the measurement values converted from the measurement values of the whole blood diluted solution (see table 7) of the examinees (samples). In this graph, when an approximation straight line (solid line) of the plots was drawn, the approximation straight line had an inclination of 0.9718, and a quite small intercept. In view of this, it can be said that the measurement value of the plasma diluted solution and the measurement value of the whole blood diluted solution after conversion are substantially equal to each other. In addition, it can be said that the conversion coefficient is different among the examinees (samples).

Table 8 shows the hematocrit value calculated from the Δ plasmon scattering light quantity, the hematocrit value calculated from the Δ plasmon resonance angle, and the hematocrit value measured by the micro hematocrit method of the samples. It can be said from table 8 that the hematocrit value calculated from the Δ plasmon scattering light quantity and the hematocrit value calculated from Δ plasmon resonance angle are substantially equal to the hematocrit value measured by the micro hematocrit method.

TABLE 8

| Sample | Δ Plasmon scattering light quantity (%) | Δ Plasmon Resonance angle (%) | Micro Hematocrit method (%) |
| --- | --- | --- | --- |
| A | 44.8 | 42.6 | 45 |
| B | 41.1 | 38.6 | 42 |
| C | 47.5 | 44.9 | 48 |
| D | 42.8 | 40.5 | 43 |
| E | 46.8 | 44.9 | 47 |
| F | 40.1 | 38.6 | 40 |

5. Type of Samples

The above-described tripled diluted solutions of whole blood and tripled diluted solutions of plasma were prepared as samples. With use of SPFS device 100 illustrated in FIG. 1, the plasmon scattering light quantity and the plasmon resonance angle in the state where the sample is introduced were measured and the Δ plasmon scattering light quantity and the Δ plasmon resonance angle were acquired for each sample. The Δ plasmon scattering light quantity of each sample is shown in table 9. In addition, the Δ plasmon resonance angle of each sample is shown in table 10.

TABLE 9

| Sample | Δ Plasmon scattering light quantity of whole blood diluted solution (count) | Δ Plasmon scattering light quantity of plasma diluted solution (count) |
| --- | --- | --- |
| A | 12556 | 469 |
| B | 11458 | −385 |
| C | 13358 | 138 |
| D | 11963 | 1308 |
| E | 13150 | −510 |
| F | 11161 | 87 |

TABLE 10

| Sample | Δ Plasmon Resonance angle of whole blood diluted solution (°) | Δ Plasmon resonance angle of plasma diluted solution (°) |
| --- | --- | --- |
| A | 1.954 | 0.03 |
| B | 1.768 | 0.01 |
| C | 2.061 | 0.05 |
| D | 1.856 | 0.00 |
| E | 2.061 | −0.03 |
| F | 1.768 | 0.00 |

Figure 6A:
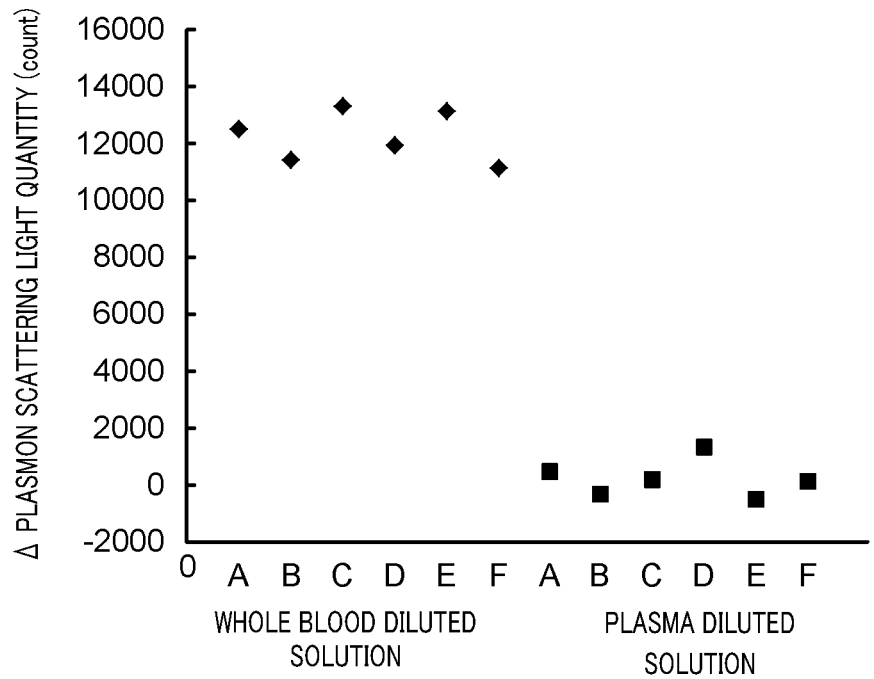
FIG. 6A is a graph showing the Δ plasmon scattering light quantity of whole blood diluted solution and plasma diluted solution.
Figure 6B:
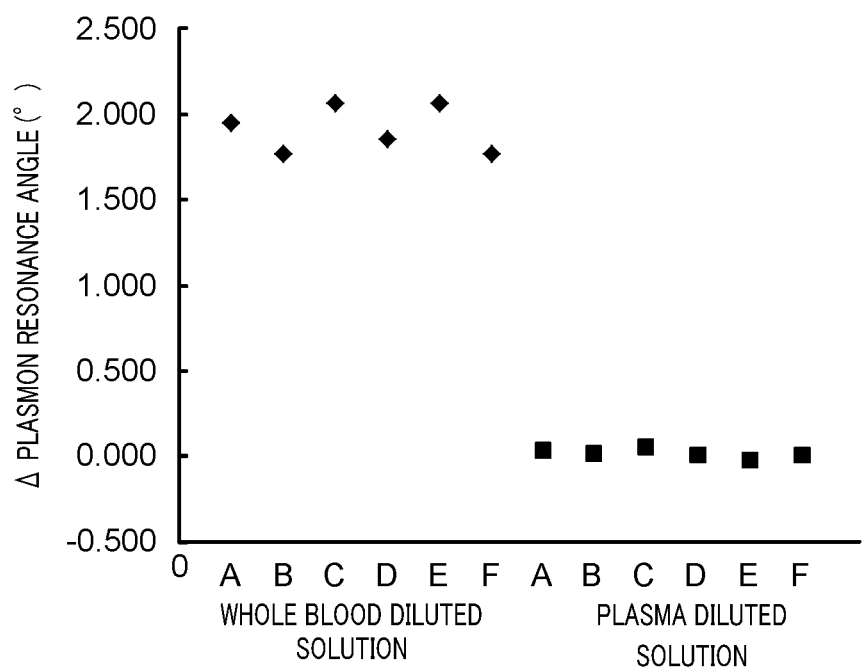
FIG. 6B is a graph showing Δ plasmon resonance angle of whole blood diluted solution and plasma diluted solution.

FIG. 6A is a graph showing the Δ plasmon scattering light quantity of the whole blood diluted solution and the plasma diluted solution (see table 9) of the examinees (samples). FIG. 6B is a graph showing the Δ plasmon resonance angle of the whole blood diluted solution and the plasma diluted solution (see table 10) of the examinees (samples). It can be said from the graphs that the Δ plasmon scattering light quantity and the Δ plasmon resonance angle are quite different between the whole blood (diluted solution) and the plasma (diluted solution) even in the same examinee. Accordingly, it can be said that whether a sample is a sample containing whole blood (blood cell component) can be determined by measuring the Δ plasmon scattering light quantity or the Δ plasmon resonance angle of the sample.

This application is entitled to and claims the benefit of Japanese Patent Application No. 2014-033961 filed on Feb. 25, 2014, the disclosure each of which including the specification, drawings and abstract is incorporated herein by reference in its entirety.

INDUSTRIAL APPLICABILITY

The measurement method and the measurement device according to the embodiment of the present invention can measure measurement object substances in blood with high reliability, and therefore are suitable for laboratory tests and the like, for example.

REFERENCE SIGNS LIST

10 Measurement chip
20 Prism
21 Incidence surface
22 Film formation surface
23 Emission surface
30 Metal film
40 Channel closure
41 Channel
100 SPFS device 110 Excitation light irradiation unit
111 Light source unit
112 Angle adjustment mechanism
113 Light source control section
120 Reflection light detection unit
121 Light receiving sensor
122 Angle adjustment mechanism
123 Sensor control section
130 Fluorescence detection unit
131 Light reception unit
132 Position switching mechanism
133 Sensor control section
134 First lens
135 Optical filter
136 Second lens
137 Light receiving sensor
140 Liquid feed unit
141 Liquid chip
142 Syringe pump
143 Liquid feed pump drive mechanism
144 Syringe
145 Plunger
150 Conveyance unit
151 Conveyance stage
152 Chip holder
160 Control section
α Excitation light
β Reflection light
γ Fluorescence
δ Plasmon scattering light

The invention claimed is:

1. A method of measuring an amount of a measurement object substance in a sample containing at least a part of blood by utilizing surface plasmon resonance, the method comprising:
   coupling a measurement object substance contained in the sample and a capturing body by supplying the sample onto a metal film of a measurement chip, the measurement chip including a prism having an incidence surface and a film formation surface, the metal film disposed on the film formation surface, and the capturing body fixed on the metal film;
   irradiating the metal film with excitation light from the prism side in a state where the sample is present on the metal film and measuring a quantity of excitation light reflected by the film formation surface, a resonance angle of the excitation light, a quantity of plasmon scattering light or an enhanced angle of the excitation light to determine whether the sample is whole blood or diluted solution of whole blood with use of an obtained measurement value, and, when the sample is determined to be whole blood or diluted solution of whole blood, acquire a hematocrit value of the whole blood with use of the obtained measurement value;
   irradiating the metal film with excitation light from the prism side in a state where the measurement object substance and the capturing body are coupled together and the sample is not present on the metal film and measuring a quantity of fluorescence emitted from a vicinity of a surface of the metal film which faces away from the prism or a quantity of excitation light reflected by the film formation surface to acquire a first signal value representing an amount of the measurement object substance in the sample; and,
   when the sample is determined to be whole blood or diluted solution of whole blood, converting the first signal value to a second signal value representing an amount of the measurement object substance in the liquid component of the sample with use of the hematocrit value of the whole blood.

2. The method according to claim 1, wherein,
   when converting the first signal value to the second signal value,
   the first signal value is converted to the second signal value by multiplying the first signal value by conversion coefficient $c_1$ of Expression (1) when the sample is whole blood which is not diluted, and
   the first signal value is converted to the second signal value by multiplying the first signal value by conversion coefficient $c_2$ of Expression (2) when the sample is diluted solution of whole blood, $$c_1 = \frac{1}{\left(1 - \frac{Ht}{100}\right)} \quad (1)$$

$$c_2 = \frac{(df - 1) + \left(1 - \frac{Ht}{100}\right)}{df\left(1 - \frac{Ht}{100}\right)} \quad (2)$$

where Ht is the hematocrit value, and df is a dilution ratio of the diluted solution.

3. A measurement device configured to measure an amount of a measurement object substance in a sample containing at least a part of blood by utilizing surface plasmon resonance, the measurement device comprising:
   a holder configured to hold a measurement chip including a prism having an incidence surface and a film formation surface, a metal film disposed on the film formation surface, and a capturing body disposed on the metal film;
   an excitation light irradiation section configured to emit excitation light toward the incidence surface;
   a light detection section configured to detect a quantity of light emitted from a vicinity of a surface of the metal film which faces away from the prism, or a quantity of excitation light reflected by the film formation surface of the prism;
   a processing section configured to determine whether the sample is whole blood or diluted solution of whole blood from a detection result of the light detection section, and calculate a first signal value representing an amount of the measurement object substance in the sample from the detection result of the light detection section, wherein, when the sample is determined to be whole blood or diluted solution of whole blood, the processing section calculates a hematocrit value of the whole blood from the detection result of the light detection section and converts the first signal value to a second signal value representing an amount of the measurement object substance in the liquid component of the sample with use of the hematocrit value of the whole blood, wherein:
   the processing section determines whether the sample is whole blood or diluted solution of whole blood with use of a quantity of excitation light reflected by the film formation surface and measured by the light detection section, a resonance angle of the excitation light measured by the light detection section, a quantity of plasmon scattering light measured by the light detection section or an enhanced angle of the excitation light measured by the light detection section when the excitation light irradiation section irradiates the metal film with excitation light from the prism side in a state where the sample is present on the metal film; and, when the sample is determined to be whole blood or diluted solution of whole blood, the processing section acquires a hematocrit value of the whole blood with use of the quantity of the excitation light reflected by the film formation surface and measured by the light detection section, the resonance angle of the excitation light measured by the light detection section, the quantity of the plasmon scattering light measured by the light detection section or the enhanced angle of the excitation light measured by the light detection section.

4. The measurement device according to claim 3, wherein the processing section converts the first signal value to the second signal value by multiplying the first signal value by conversion coefficient $c_1$ of Expression (1) when the sample is whole blood which is not diluted, and converts the first signal value to the second signal value by multiplying the first signal value by conversion coefficient $c_2$ of Expression (2) when the sample is diluted solution of whole blood, $$c_1 = \frac{1}{\left(1 - \frac{Ht}{100}\right)} \quad (1)$$

$$c_2 = \frac{(df - 1) + \left(1 - \frac{Ht}{100}\right)}{df\left(1 - \frac{Ht}{100}\right)} \quad (2)$$

where Ht is the hematocrit value, and df is a dilution ratio of the diluted solution.

* * * * *